(12) United States Patent
Kien

(10) Patent No.: US 7,947,014 B2
(45) Date of Patent: May 24, 2011

(54) RELIEF VALVE FOR USE WITH A BALLOON CATHETER

(76) Inventor: Tai Kien, Lowell, MA (US)

( * ) Notice: Subject to any disclaimer, the term of this patent is extended or adjusted under 35 U.S.C. 154(b) by 0 days.

(21) Appl. No.: 12/454,248

(22) Filed: May 15, 2009

(65) Prior Publication Data

US 2010/0292640 A1 Nov. 18, 2010

(51) Int. Cl.
*A61M 1/00* (2006.01)
*A61M 29/00* (2006.01)

(52) U.S. Cl. ............ 604/99.02; 604/118; 604/121; 604/920; 604/99.01; 604/99.04; 604/99.03

(58) Field of Classification Search ............ 604/533, 604/537, 534, 539, 99.01–99.04, 118, 905, 604/920, 921, 121; 128/912
See application file for complete search history.

(56) References Cited

U.S. PATENT DOCUMENTS

| | | | | |
|---|---|---|---|---|
| 3,985,141 A | * | 10/1976 | Stanley et al. | ............ 128/207.15 |
| 4,044,793 A | * | 8/1977 | Krueger et al. | ............... 137/881 |
| 4,147,170 A | * | 4/1979 | Taylor | ....................... 128/207.15 |
| 4,403,988 A | * | 9/1983 | Binard et al. | .................. 604/118 |
| 2010/0217064 A1 | * | 8/2010 | Benson et al. | .................... 600/7 |

* cited by examiner

*Primary Examiner* — Nicholas D Lucchesi
*Assistant Examiner* — Leah Stohr
(74) *Attorney, Agent, or Firm* — William Nitkin

(57) ABSTRACT

A relief valve incorporated within a Luer connector regulates the amount of air pressure applied by a syringe to a balloon at the end of a catheter to prevent bursting of the balloon.

3 Claims, 2 Drawing Sheets

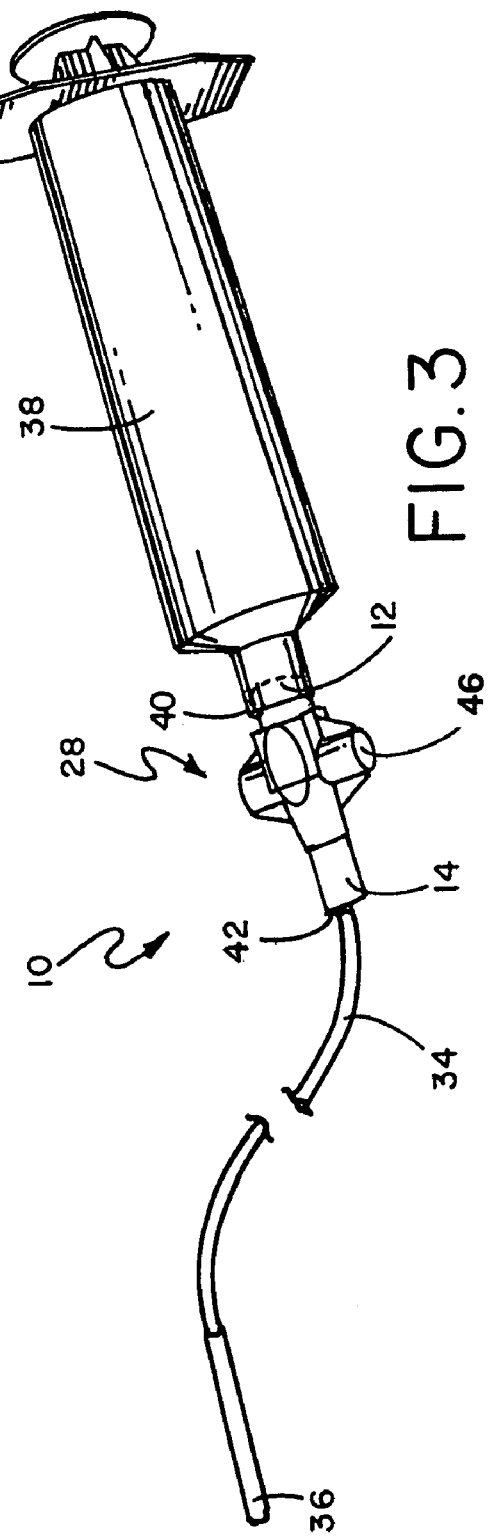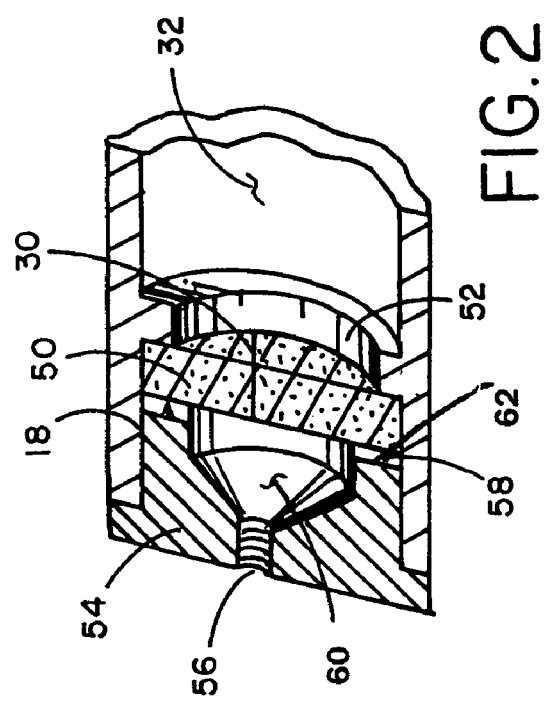

RELIEF VALVE FOR USE WITH A BALLOON CATHETER

BACKGROUND OF THE INVENTION

1. Field of the Invention

The device of this invention resides in the field of balloon catheters which are inflated by air pressure through a tube, such air pressure generally provided by a syringe, and more particularly relates to a Luer connector that incorporates a relief valve therein to control and regulate the amount of air pressure going to the balloon portion of the catheter to prevent too much air pressure from bursting the balloon.

2. Description of the Prior Art

Balloon catheters are well known in the medical field and generally have a tube leading to an inflatable balloon at the end thereof which tube and balloon are inserted into a portion of a patient's body. Air is typically delivered from a syringe, through the Luer connector and into the tube to inflate the balloon to retain the catheter in its desired position in the body. Over inflation of the catheter balloon can cause the balloon to burst which action can have undesirable consequences, such as releasing the retention of the catheter, leaving balloon debris within the body as well as creating other medical issues. It is thus desirable to avoid inflating the balloon beyond what its balloon walls can withstand to prevent its bursting. It is currently very difficult to control the amount of air pressure that one is applying to the balloon from the syringe as the inflated balloon is no longer visible once it is positioned within the patient's body.

SUMMARY OF THE INVENTION

It is an object of this invention to provide a relief valve incorporated within a Luer connector between the air supply syringe and the tube leading to the balloon catheter to prevent excess air pressure from bursting the balloon of the catheter. To this end the device of this invention provides first and second air escape valves which, when the air pressure passing through the connector exceeds a predetermined pressure level, allows such excess air pressure to escape through the first and second air escape valves in the connector. The escape of excess air pressure keeps the air pressure at a safe level to prevent the bursting of the catheter's balloon.

BRIEF DESCRIPTION OF THE DRAWINGS

FIG. 2 illustrates a perspective view of a portion of an air escape valve.

FIG. 3 illustrates a perspective view of the relief valve of this invention in a Luer connector attached to a syringe at one end and to a tube at its other end extending to a balloon catheter.

DESCRIPTION OF THE PREFERRED EMBODIMENT(S)

Figure 1:
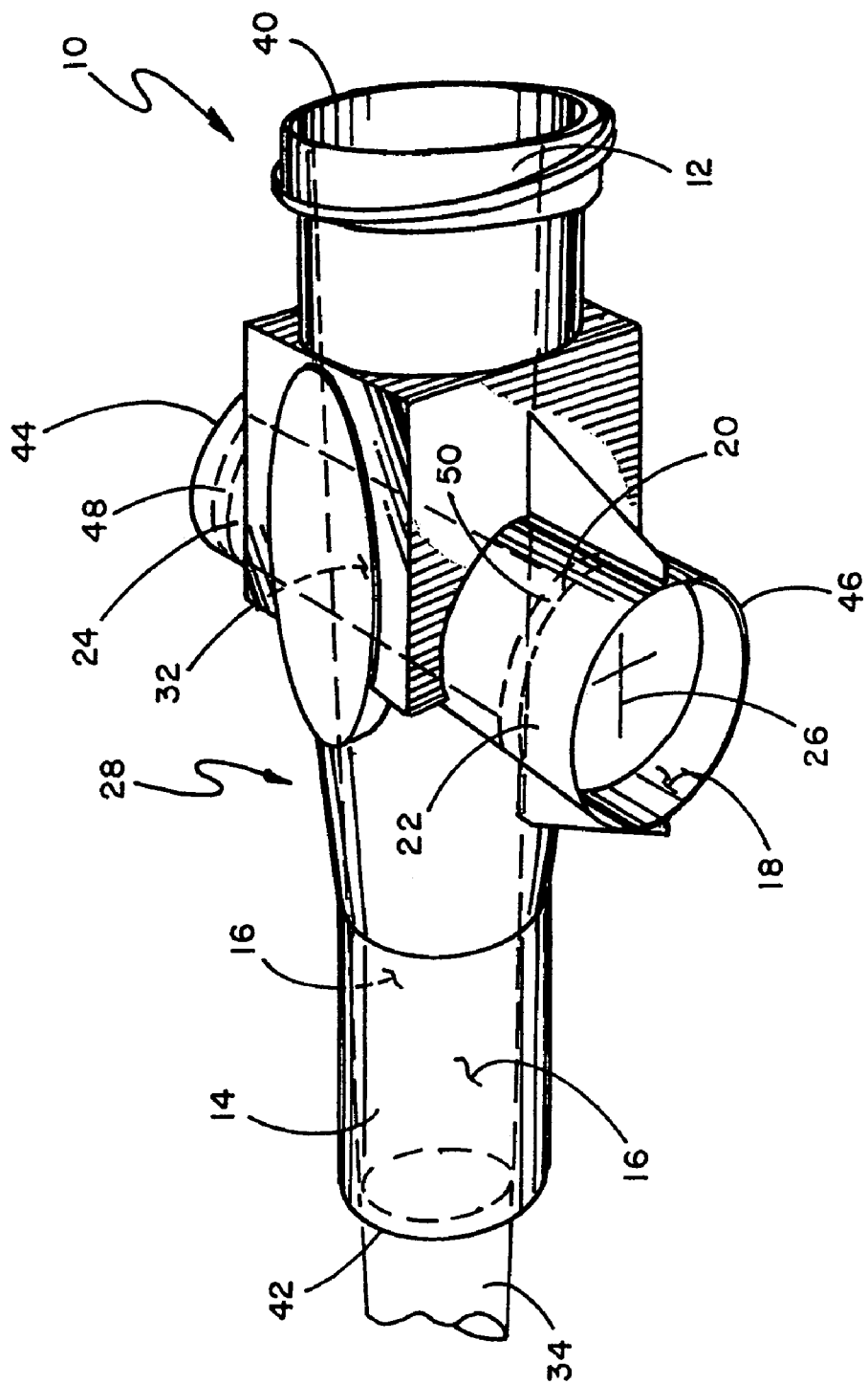
FIG. 1 illustrates a perspective view of the relief valve of this invention within a Luer connector.

FIG. 1 illustrates a close-up view of relief valve 10 of this invention within Luer connector 28 which at a first end 40 has male Luer lock 12 and at its second end 42 has a tube engagement portion 14 which, as also seen in FIG. 3, engages to tube 34 which extends to deflated balloon 36 as part of the catheter that is inserted into a patient's body. Balloon 36 is then inflated by air pressure from syringe 38 through Luer connector 28 through tube 34 into balloon 36 such that the inflated balloon then retains the catheter in place within the patient's body. Extending the length of Luer connector 28 is main passage 16. Extending transversely to main passage 16 is vent passage 32 having first air escape valve 24 at first end 44 and a second air escape valve 22 at second end 46. Vent passage 32 which is formed of first and second substantially cylindrical members, such as member 20, is in communication with main passage 16 such that air pressure within main passage 16 also extends to and is equal with the air pressure within vent passage 32. First and second air escape valves 24 and 22 are disposed, respectively, near first and second ends 44 and 46 of vent passage 32 and have, respectively, first and second diaphragm 48 and 50 which can be disk-like, each diaphragm made of a resilient material, such as silicon or latex and each diaphragm having a vent, such as second valve escape cross slit 26 shown in FIG. 1. The vents can be comprised of at least one slit defined in each diaphragm. The material of the diaphragm must be of sufficient resiliency that it will resist the passage of air therethrough up to a predetermined air pressure. The resilience and thickness of the diaphragms material can differ for different predetermined air pressures. Although cross slits comprise the vents in the diaphragms illustrated in FIGS. 1 and 2, other types, shapes and sizes of vents can be utilized which will open and allow air to pass therethrough when a predetermined air pressure is reached. When the predetermined air pressure is exceeded that is considered sufficient to burst balloon 36, the air pressure will be lowered by the escape of air through first and second air escape valves 24 and 22, each of which has air escape slits, such as second valve cross slits 30 in second air escape valve 22 to reduce the air pressure in the connector/tube/balloon and prevent the bursting of balloon 36 by inadvertent application of excessive air pressure from syringe 38.

FIG. 2 illustrates a cross-sectional view through the end of second air escape valve 22, showing second diaphragm 50 supported on ledge 52 with part of cross slit 30 seen formed therein. Plug 54 holds second diaphragm 50 in place which plug has chamber 60 defined therein immediately above first valve slit 30 which opens through plug aperture 56 to the exterior of the device. Plug 54 can be generally cylindrical and can fit into the air escape valve, such as second air escape valve 22 which also can be cylindrical to receive disk-shaped second diaphragm 50 held from further inward advance within vent passage 32 by ledge 52 such that plug 54 can have a portion 62 thereof contact the opposing side of second diaphragm 50 at plug contact point 58 from that contacting ledge 52 to hold second diaphragm 50 securely in place within vent passage 32 and to allow air pressure escaping therethrough to pass through open chamber 60 to the exterior. It should be noted that first air escape valve 24, as seen in FIG. 2, can be constructed in a similar manner on the opposite first end 44 of vent passage 32.

Although the present invention has been described with reference to particular embodiments, it will be apparent to those skilled in the art that variations and modifications can be substituted therefor without departing from the principles and spirit of the invention.

I claim:

1. A Luer connector having a main passage defined therein, said main passage for positioning between a syringe and a catheter having a tube with a balloon at the end thereof, said main passage extending axially through said Luer connector for interconnecting said syringe to said tube extending to said balloon, comprising:

a relief valve incorporated into said Luer connector, said relief valve for regulating the amount of air pressure going to said balloon at the end of said catheter by allowing air to escape therethrough above a predetermined air pressure to prevent said balloon from bursting, wherein said relief valve is incorporated into a vent passage having first and second ends defined within said Luer connector, said vent passage disposed transverse to said main passage, said relief valve further comprising first and second air escape valves defined within, respectively, said first and second ends of said vent passage; and wherein said first and second air escape valves contain, respectively, first and second diaphragms having air escape means defined therein for allowing the passage of air therethrough above a predetermined air pressure level within said main passage and said vent passage of said Luer connector.

2. A Luer connector having a main passage defined therein, said main passage for positioning between a syringe and a catheter having a tube with a balloon at the end thereof, said main passage extending axially through said Luer connector for interconnecting said syringe to said tube extending to said balloon, comprising:

a relief valve incorporated into said Luer connector, said relief valve for regulating the amount of air pressure going to said balloon at the end of said catheter by allowing air to escape therethrough above a predetermined air pressure to prevent said balloon from bursting, wherein said relief valve is incorporated into a vent passage having first and second ends defined within said Luer connector, said vent passage disposed transverse to said main passage, said relief valve further comprising first and second air escape valves defined within, respectively, said first and second ends of said vent passage;

wherein said first and second air escape valves contain, respectively, first and second diaphragms having air escape means defined therein for allowing the passage of air therethrough above a predetermined air pressure level within said main passage and said vent passage of said Luer connector; and wherein said vent passage is formed with first and second substantially cylindrical members disposed, respectively, at said first and second ends of said vent passage, said first and second cylindrical members each having an outer end and having, respectively, first and second diaphragms disposed, respectively, within said first and second cylindrical members near said outer ends, said first and second diaphragms each having at least one valve slit defined therein, said valve slits forming air escape means at said predetermined air pressure.

3. The device of claim 2 further including:

first and second ledge members defined, respectively, within said first and second ends of said cylindrical members for receiving said first and second diaphragms thereagainst; and first and second plug members for insertion, respectively, into said first and second ends, respectively, of said first and second cylindrical members for retaining said first and second diaphragms in position, respectively, against said first and second ledge members, said first and second plug members each having a chamber defined therein positioned above said valve slit, said chamber being open to said exterior of said relief valve for escape of air therethrough when said air pressure exceeds said predetermined air pressure level of said relief valve, said air passing through said valve slits in said first and second diaphragms to said exterior of said relief valve.

* * * * *